(12) United States Patent
Martinoty et al.

(10) Patent No.: US 7,784,329 B2
(45) Date of Patent: Aug. 31, 2010

(54) PIEZO-RHEOMETRIC MEASURING CELL AND CORRESPONDING PIEZO-RHEOMETER

(75) Inventors: Philippe Martinoty, Strasbourg (FR); Dominique Collin, Geispoisheim (FR)

(73) Assignee: Universite Louis Pasteur (Etablissement Public a Caractere Scientifique, Culturel et Professionnel), Strasbourg (FR)

( * ) Notice: Subject to any disclaimer, the term of this patent is extended or adjusted under 35 U.S.C. 154(b) by 399 days.

(21) Appl. No.: 11/632,843

(22) PCT Filed: Jul. 21, 2005

(86) PCT No.: PCT/FR2005/001891

§ 371 (c)(1),
(2), (4) Date: Oct. 11, 2007

(87) PCT Pub. No.: WO2006/018516

PCT Pub. Date: Feb. 23, 2006

(65) Prior Publication Data

US 2008/0236255 A1   Oct. 2, 2008

(30) Foreign Application Priority Data

Jul. 22, 2004   (FR) .................................. 04 08128

(51) Int. Cl.
*G01N 11/00*   (2006.01)

(52) U.S. Cl. .................... 73/54.01; 73/54.39; 73/54.41; 73/64.53

(58) Field of Classification Search ................ 73/54.01, 73/54.04, 54.23, 54.24, 54.41, 64.53
See application file for complete search history.

(56) References Cited

U.S. PATENT DOCUMENTS 3,194,064 A   7/1965   Miles (Continued)

FOREIGN PATENT DOCUMENTS

EP   0 950 889   10/1999

(Continued)

OTHER PUBLICATIONS

Physical Review Letters, vol. 45, No. 17, Oct. 27, 1980, pp. 1418-1421, XP002318931, the whole document.

(Continued)

*Primary Examiner*—David A. Rogers
(74) *Attorney, Agent, or Firm*—Young & Thompson (57) ABSTRACT

The invention relates to a piezo-rheometric measuring cell for shear or compression measurement, essentially comprising two sample holder plates, with the sample for analysis between the same in solid, liquid or intermediate form, piezo-electric ceramic elements on the faces of the plates opposite to the faces in contact with the sample and a construction forming the housing and compressing the arrangement of plates and ceramic elements, one or more ceramics called emitter, being connected to one of the two plates or the emitter plate and subjecting the same to shear or compression vibrations by means of an excitation signal and one or more ceramics, called receiver, being connected to the other plate or receiver plate and converting the forces to which the same is subject into a measured signal. The cell is characterized in that the emitter and receiver cell(s) are arranged such that the respective polarizations of the emitter ceramic (4) and the receiver ceramic (4'), or the respective resultant polarizations of the emitter ceramics (4) and the receiver ceramics (4') are parallel and in the same direction. Said cell (1) is preferably portable and permits measurements with variation in temperature and/or pressure.

32 Claims, 7 Drawing Sheets

U.S. PATENT DOCUMENTS

| | | | | |
|---|---|---|---|---|
| 4,312,228 | A * | 1/1982 | Wohltjen | 73/597 |
| 4,779,452 | A * | 10/1988 | Cohen-Tenoudji et al. | 73/54.41 |
| 5,433,112 | A * | 7/1995 | Piche et al. | 73/597 |
| 5,739,432 | A * | 4/1998 | Sinha | 73/579 |
| 5,750,884 | A | 5/1998 | Field et al. | |
| 6,668,622 | B2 * | 12/2003 | Hajduk et al. | 73/54.37 |
| 6,978,662 | B2 * | 12/2005 | Platzek et al. | 73/54.42 |
| 7,328,604 | B2 * | 2/2008 | DeNatale et al. | 73/54.02 |
| 7,398,685 | B2 * | 7/2008 | Itoh et al. | 73/599 |
| 7,484,414 | B2 * | 2/2009 | Priev et al. | 73/649 |
| 7,578,172 | B2 * | 8/2009 | Cho | 73/54.24 |
| 2003/0062564 | A1 * | 4/2003 | Kobayashi et al. | 257/306 |
| 2004/0080038 | A1 * | 4/2004 | Chew et al. | 257/691 |
| 2006/0065045 | A1 * | 3/2006 | Borwick et al. | 73/54.23 |
| 2007/0180938 | A1 * | 8/2007 | Baroni et al. | 73/866 |

FOREIGN PATENT DOCUMENTS

FR  2588664 A1 * 4/1987

OTHER PUBLICATIONS

Physical Review Letters, vol. 39, No. 21, Oct. 21, 1977, pp. 1346-1349, XP002318932, the whole document.

Macromolecules, vol. 32, No. 14, 1999, pp. 45666-4574, XP002318946, the whole document.

* cited by examiner

PIEZO-RHEOMETRIC MEASURING CELL AND CORRESPONDING PIEZO-RHEOMETER

This invention relates to the field of devices and instruments for measuring physical and mechanical characteristics of solid, liquid or intermediate materials such as gels and elastomers, in particular those relating to rheology.

This invention has as its object an improved piezorheometer cell, a measuring instrument of the piezorheometer type, and a measuring process using this instrument.

Shear or compression piezorheometers that comprise a measuring cell that essentially consists of, on the one hand, two sample-holder blades that clamp between them the solid, liquid or intermediate-type sample to be analyzed, and, on the other hand, piezoelectric ceramic elements relative to the faces of the blades that are opposite to the faces that are in contact with the sample, and, finally, a box-forming frame that keeps the arrangement of blades and ceramic elements compressed are already known. One or more of the ceramic element(s) is (are) tied or stuck to one of the two blades or an emitting blade and subjects (subject) the latter to shear or compression vibrations under the action of an excitation signal that is delivered by a feed chain, and one or more ceramic element(s) is (are) tied or stuck to the other blade or receiving blade and transforms (transform) the constraints or stress to which the latter is subjected into a measuring signal.

It thus is possible to define one or more emitter or emission ceramic element(s) and one or more receptor or receiving ceramic element(s).

Figure 1:
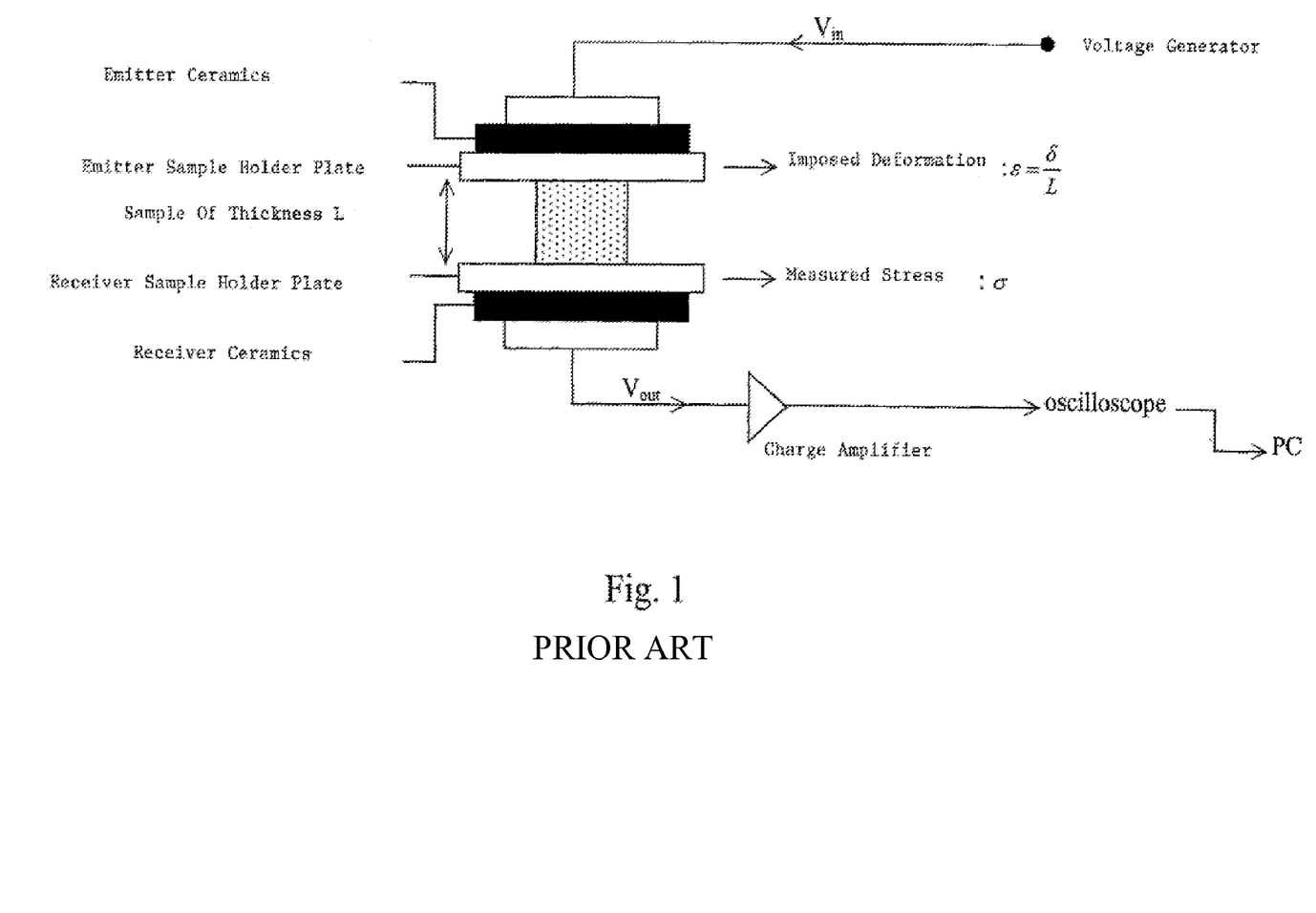
FIG. 1 is a schematic view of a known piezorheometer.

A known piezorheometer that comprises a cell of the above-mentioned type (with one single ceramic element per blade) is shown in FIG. 1 of the accompanying drawings.

Two examples of use of such a known piezorheometer for determining characteristics of different materials are described in the following publications: "Influence of Molecular Parameters on the Elastic and Viscoelastic Properties of Side-Chain Liquid Crystalline Elastomers," J. J. Zanna et al., Macromolecules, Vol. 35, No. 14, pages 5459-5965, 2002; "Rheology of Liquid Crystalline Elastomers in their Isotropic and Smectic A State," J. Weilepp, Macromolecules, Volume 32, No. 14, pages: 4566-4574, 1999.

Such a piezorheometer is, as FIG. 1 shows, a plate-plate rheometer working either in the shear mode or in the compression mode, according to the types of piezoelectric ceramic elements that are used.

Its principle consists, according to the first variant, in imposing a very small deformation or strain on a solid or liquid sample by means of a piezoelectric ceramic that vibrates in the shear mode (i.e., in a direction that is parallel to the plane of the rheometer) and stuck on or cohesive with the emitting sample-holder blade and in measuring the amplitude and the phase of the stress transmitted through the sample with a second piezoelectric ceramic that is stuck on or cohesive with the receiving sample-holder blade. The ratio of the constraint to the deformation or stress over strain ratio provides the complex shear modulus $G=G'+iG''$ of the sample (or its complex viscosity $\eta=\eta'+i\eta''$).

In the case where the emitting and receiving ceramics vibrate in compression (i.e., in a direction that is perpendicular to the plane of the rheometer), the stress over strain ratio provides either the complex viscosity in the case of low-viscosity fluids (such as water or biological substances) thanks to a geometric amplification factor, or the Young module (E or Z) in the case of soft solids, such as gels or elastomers.

The sample is placed between two blades, for example silica glass, whereby each of the blades is stuck to one of the ceramics.

The excitation of the emitter piezoelectric ceramic element or the emitting ceramic is carried out by means of a signal with variable voltage, for example sinusoidal, delivered by a function generator or the like.

The variable voltage is transformed by this moving ceramic element or emitting ceramic in a displacement $\delta$ that is transmitted to the sample via the emitting sample-holder blade. The sample, with a thickness L, is then subjected to a strain $\epsilon=\delta/L$, which induces a stress $\sigma$ on the receiving ceramic. This stress creates charges in the ceramic that are integrated via a charge amplifier and transformed into a sinusoidal voltage. The input and output voltages, $V_{in}$ and $V_{out}$, as well as the phase shift $\varphi$ between the two signals are measured with a suitable device, for example an oscilloscope that is equipped with a Fourier transform module. These data are transmitted to a PC (personal computer)-type computer, programmed to calculate the complex shear modulus G.

The real part G' and the imaginary part G'' of the complex shear modulus G are provided by:

$$G'(\omega) = \frac{L}{A_V d_{15}^2 S} \times \frac{V_{out}(\omega)}{V_{in}(\omega)} \times \cos\varphi(\omega)$$

$$G''(\omega) = \frac{L}{A_V d_{15}^2 S} \times \frac{V_{out}(\omega)}{V_{in}(\omega)} \times \sin\varphi(\omega)$$

In these formulas, S is the surface area of the sample in contact with the blades, $A_V$ is the gain of the charge amplifier, and $d_{15}$ is the piezoelectric constant in question.

In the case of the compression, the ratio $Z=\sigma/\epsilon$ is provided by:

$$Z'(\omega) = \frac{L}{A_V d_{33}^2 S} \times \frac{V_{out}(\omega)}{V_{in}(\omega)} \times \cos\varphi(\omega)$$

$$Z''(\omega) = \frac{L}{A_V d_{33}^2 S} \times \frac{V_{out}(\omega)}{V_{in}(\omega)} \times \sin\varphi(\omega)$$

These formulas are identical to the preceding formulas, with the exception of the piezoelectric constant that is now $d_{33}$.

It should be noted that these piezorheometers can also function by using excitations of different shapes: triangles, ramps, gaps, etc.

However, within the framework of the use and the implementation of the above-mentioned known piezorheometer, the inventors noted a certain number of drawbacks and limitations, restricting the application of this type of instrument, as well as the quality and the reliability of the measurements provided.

A major drawback that is noted by the inventors is tied to the existence of an electrostatic coupling between the emitting ceramic and the receiving ceramic. This effect results from the very small distance (generally at most several millimeters) separating these ceramics and is at the origin of a parasitic radiated signal.

Thus, the first object of the invention is to propose a solution that makes it possible to reduce in particular, and even to virtually eliminate, said parasitic signal and to make it possible to differentiate the latter from the measuring signal associated with the mechanical response of the sample.

For this purpose, the object of the invention is a shear or compression piezorheometer cell, essentially consisting of, on the one hand, two sample-holder blades that clamp between them the solid, liquid or intermediate-type sample to be analyzed, and, on the other hand, piezoelectric ceramic elements relative to the faces of the blades that are opposite to the faces in contact with the sample, and, finally, a frame that keeps the arrangement of blades and ceramic elements compressed, whereby at least one ceramic element, denoted emitting ceramic below, is stuck to or made cohesive with one of the two blades or emitting blade and subjects the latter to shear or compression vibrations under the action of an excitation signal, and whereby at least one ceramic element, denoted receiving ceramic below, is stuck to or made cohesive with the other blade or receiving blade and transforms the constraints or stress to which the latter is subjected into a measuring signal, a cell that is characterized in that the emitting and receiving ceramics are placed so that the respective polarizations of the emitting ceramic and the receiving ceramic, or the respective resulting polarizations of the emitting ceramics and receiving ceramics are parallel and of the same direction (orientation).

In addition, it may be provided that the sample-holder blades have an increased thickness, greater than that necessary to make them strong and rigid enough to perform their function and that one or more shield part(s) designed to limit the electrostatic radiation and the electrostatic coupling that result between the emitting ceramic(s) and the receiving ceramic(s) are mounted in the frame.

The invention will be better understood, thanks to the description below, which relates to a preferred embodiment, provided by way of nonlimiting example and explained with reference to the accompanying schematic drawings, in which.

Figure 2:
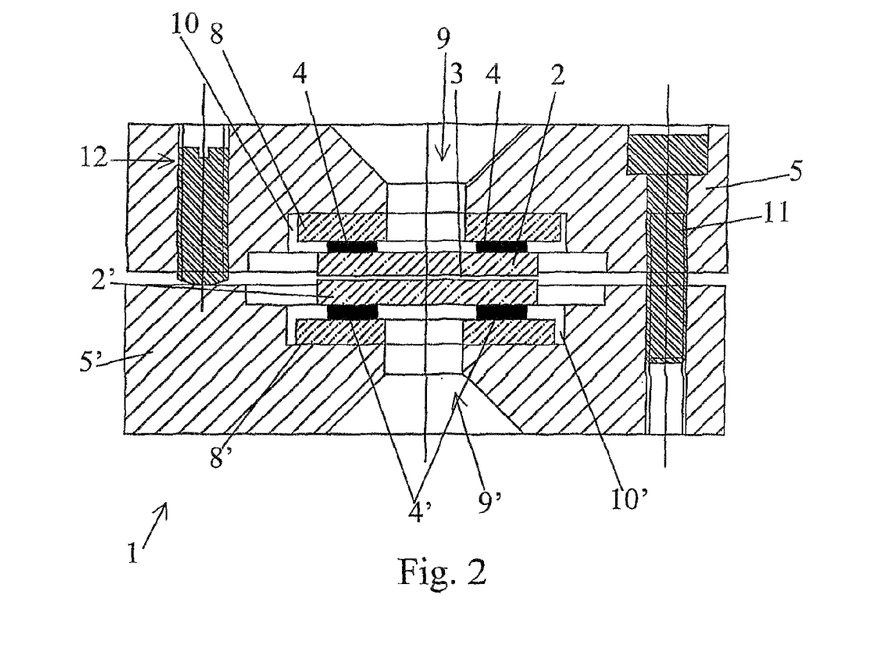
FIG. 2 is a cutaway view of a measuring cell according to the invention.
Figure 9A:
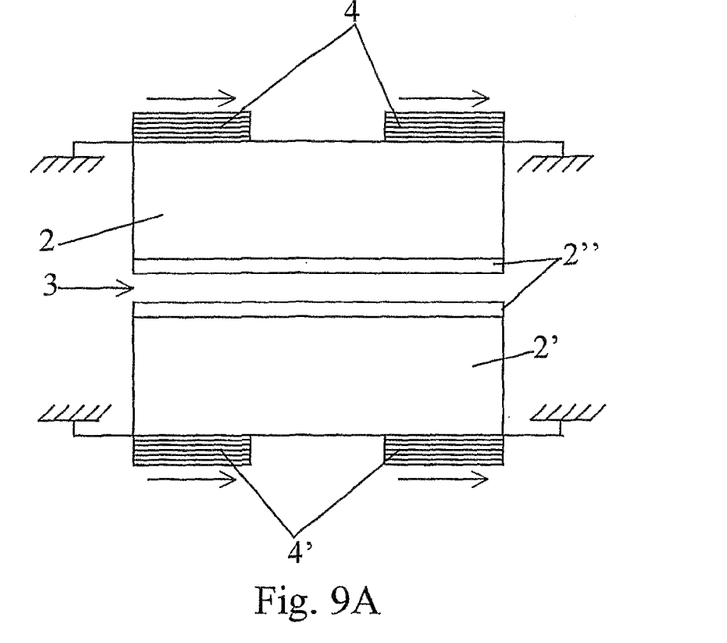
FIGS. 9A and 9B are partial schematic representations of arrangements of two assemblies [ceramics/sample-holder blade] forming part of a measuring cell according to the invention, or a shear measuring cell and compression measuring cell, showing the polarizations of emitting and receiving ceramics.
Figure 9B:
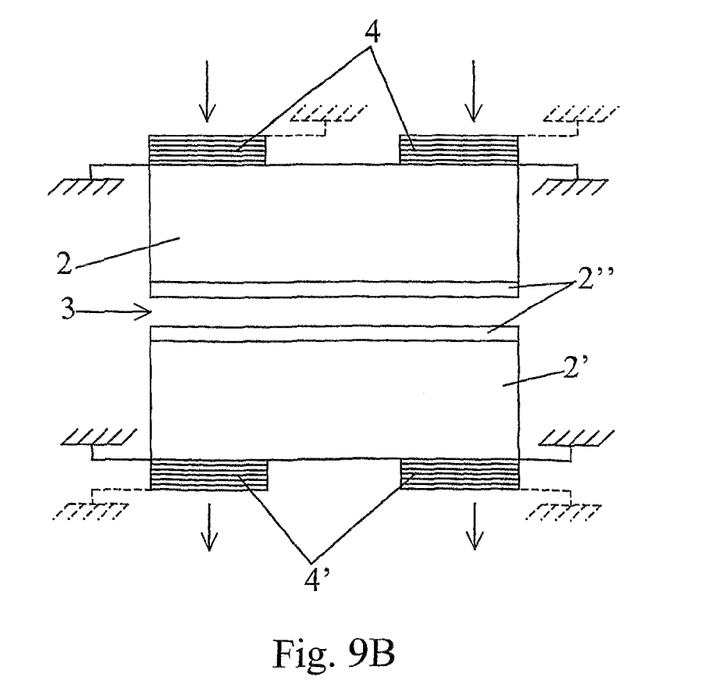
Figure 10:
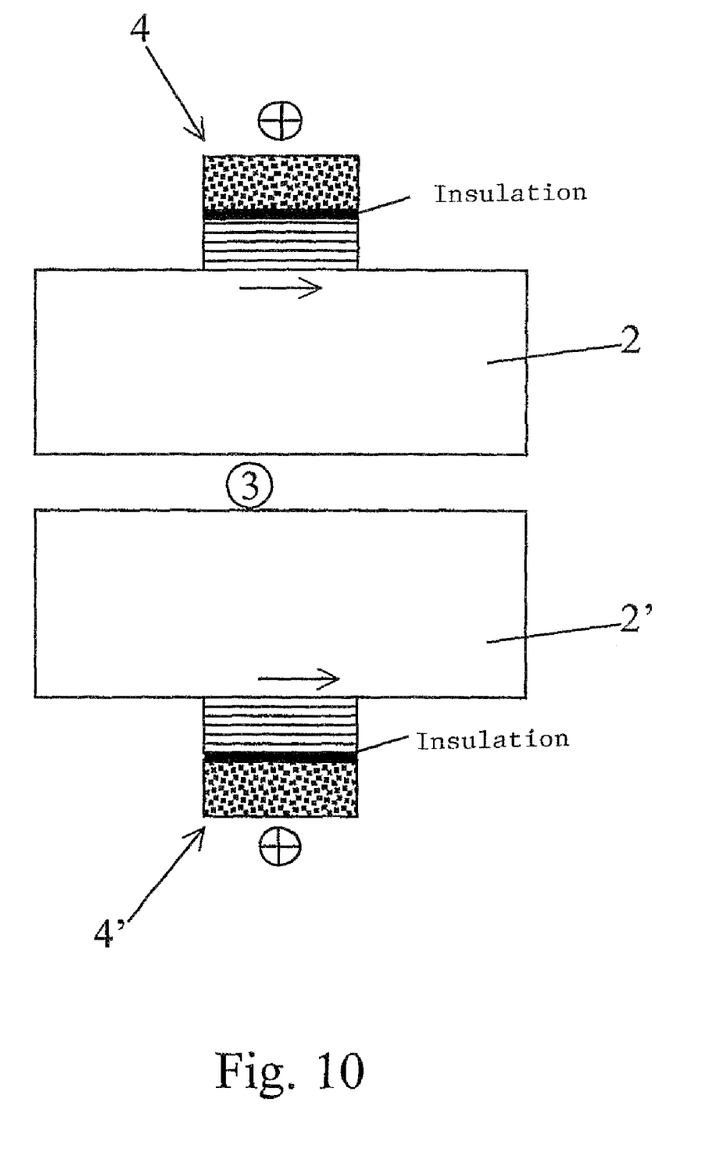
FIG. 10 is a partial schematic representation of an arrangement of two assemblies [ceramic/sample-holder blade] forming part of a shear measuring cell according to a variant of the invention.

As FIG. 2 and partially FIGS. 9A, 9B and 10 of the accompanying drawings show, the measuring cell 1 essentially consists of, on the one hand, two sample-holder blades 2 and 2' that clamp between them the solid, liquid or intermediate-type sample 3 that is to be analyzed, and, on the other hand, piezoelectric ceramic elements 4 and 4' relative to the faces of the blades 2 and 2' that are opposite to the faces in contact with the sample 3, and, finally, a frame 5, 5' that keeps the arrangement of blades 2, 2' and ceramic elements 4, 4' compressed, at least one ceramic element 4, denoted emitting ceramic below, is tied or being stuck to one of the two blades or emitting blade 2 and subjecting the latter to shear or compression vibrations under the action of an excitation signal, and whereby at least one ceramic element 4', denoted receiving ceramic below, is tied or being stuck to the other blade or receiving blade 2' and transforming the stress to which the latter is subjected into a measuring signal.

According to the invention, the emitting and receiving ceramics are placed so that the respective polarizations of the emitting ceramic 4 and the receiving ceramic 4' or the respective resulting polarizations of the emitting ceramics 4 and the receiving ceramics 4' are parallel and of the same direction.

It is understood, of course, that each of the two blades 2 and 2' can be provided with a single piezoelectric ceramic element 4 or 4' as shown in FIG. 1, or several elements 4 or 4', in particular two elements as is evident from FIG. 2 and FIGS. 9A and 9B.

In a particular way, it may be provided that in the case of a shear measuring cell 1, each ceramic element for emission 4 and for reception 4' consists of a stacking of two ceramics having orthogonal polarization directions in the median plane of said measuring cell 1, as shown in FIG. 10.

Such a stacking of crossed ceramics for emission and reception makes it possible to measure directly a possible anisotropy of the complex shear modulus on the same sample.

For the purpose of increasing the gap between emitting ceramic elements 4 and receiving ceramic elements 4' and therefore limiting the electrostatic coupling between them, it may be advantageously provided that the sample-holder blades 2, 2' have an increased thickness, greater than that necessary to make them strong and rigid enough to perform their function of holding the sample 3.

In addition, to reduce the parasitic radiation even more between emitting ceramics 4 and receiving ceramics 4', one or more shield part(s) 6 designed to limit the electrostatic radiation and the electrostatic coupling that results therefrom between the emitting ceramic(s) 4 and the receiving ceramic(s) 4', is (are) mounted in the frame 5, 5'.

Preferably, this shield part or each shield part 6 designed to reduce or to eliminate the radiation and the electrostatic coupling that results therefrom consists of a jacket, a plate or a metal blade, placed between, on the one hand, the emitting blade 2 or the receiving blade 2', and, on the other hand, the frame 5, 5'. This or these shield part(s) 6 will extend in particular above the excitation signal feed point of the emitting ceramic elements 2.

For the purpose of making it possible to adapt the measuring cell 1 to the chemical nature of the sample 3, one or each of the two sample-holder blades 2 and 2' is provided, on its face turned toward the sample 3, with a layer or a coating 2", for example in the form of an additional covering blade that is removably added or attached to this blade 2 and 2'.

These additional layers or covering blades ("overblades") can be dissolved, for example, or detached (dissolving of the holding glue) when the corresponding shell portion 5 or 5' is immersed in an adequate solvent bath (whereby this solvent is inert with regard to the other connections between the other components of the part being considered).

Preferably, at the level of their faces or faces of the additional covering blades 2", in contact with the sample 3 to be analyzed, the sample-holder blades 2 and 2' comprise a surface treatment that prevents or promotes the sliding of the sample 3 or orients the latter at the level of said faces in contact with the latter (for example, striations, grooves, roughness, or chemical treatments).

These faces can therefore be perfectly defined in terms of characteristics and properties, in particular based on the nature of the sample, the type of analysis, and the value(s) or parameter(s) to be measured.

In most of the cases, the faces of the blades 2, 2' or removable additional blades 2" that are attached to the latter will be smooth and flat.

Figure 8:
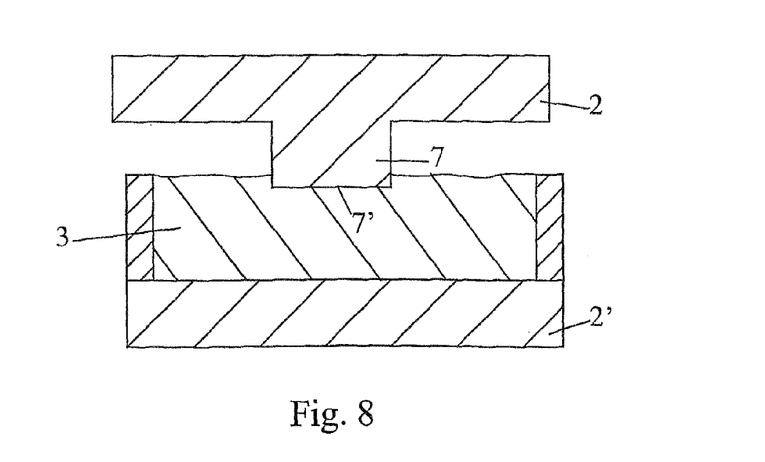
FIG. 8 is a cutaway view, on a different scale, of sample-holder blades according to a variant embodiment of the invention.

Nevertheless, according to a variant embodiment shown in FIG. 8, the emitting sample-holder blade 2 has a protuberance forming piston 7 at its face in contact with the sample 3, whereby the sample layer 3 that is located between the front face 7' of the protuberance 7 and the smooth and flat face of the receiving sample-holder blade 2' forms the analyzed sample portion.

Thus, the result is the production of a cell 1 with a reservoir, advantageously adapted to compression measurements in the aqueous systems (or in the systems that exhibit a quick evaporation) and that make it possible to take rheological measurements without using controlled-humidity chambers.

In addition, this particular conformation of the blades 2, 2' of the cell 1, makes it possible to take advantage of the geometric effects linked to the thickness difference in the mechanical response on the level of the physical execution of the measurement.

So as to obtain a compact structure with close and rigid contacts between the different constituent parts of the measuring cell 1, it is advantageously provided that the piezoelectric ceramic elements 4, 4' are added to the respective sample-holder blades 2 and 2' by gluing or welding and are each assembled with the frame 5, 5' by gluing or welding, optionally with interposition of a part for bracing and electrical insulation, the bonding and assembly adhesive(s) preserving their adhesive property and their rigidity in a temperature range of −60° C. to +180° C., preferably −100° C. to +200° C.

To make possible a specific accounting of the variations of the size of cell 1 in the processing of measuring signals, the material or materials for bonding and assembly, the material constituting the frame 5, 5', and, if necessary, the material that constitutes the parts 8 for bracing and electrical insulation all have predetermined thermal expansion/retraction factors that are essentially of the same value as the thermal expansion/retraction factor of the material that constitutes the sample-holder blades 2, 2', for example glass.

In particular, the rigidity of the various above-mentioned components should be greater than that of the material or the substance forming the sample 3.

Actually, the measurements as a function of the temperature assume that the distance between the sample-holder blades or air gap of cell 1 are not sensitive to temperature variations, this condition, which is dependent on the suitability between the expansion coefficients of the different elements that constitute the cell (glues or welding, frame, ceramic sample-holder blades), having to be verified before each thermal excursion.

Figure 3:
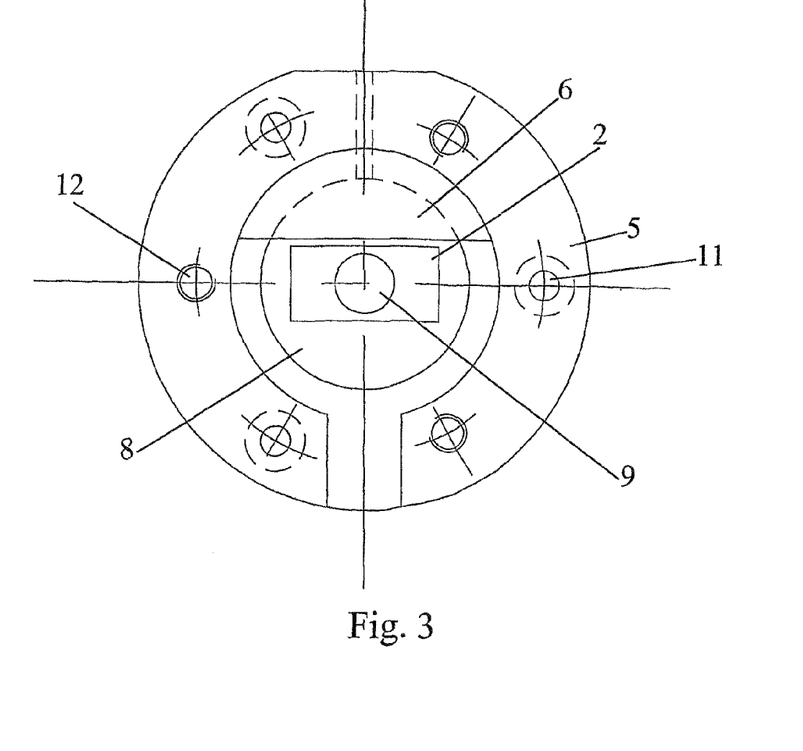
FIG. 3 is a top view of a half-shell forming part of the cell shown in FIG. 2.

According to a very advantageous characteristic of the invention, emerging from FIGS. 2 and 3 of the accompanying drawings, the assembly formed by the frame 5, 5' with, mounted therein, the piezoelectric ceramic elements 2, 2', as well as, if necessary, the shield part(s) 6 and/or the parts for bracing and electric insulation 8, has a perforated structure comprising two opposite openings 9 and 9' for observation and irradiation of the sample 3 extending respectively from the outside of the frame 5, 5' up to the sample holder blades 2, 2'.

It will thus be possible, for example, to observe the sample 3 during the imposed deformation or else to subject the entire sample 3 homogeneously to radiation, for example ultraviolet radiation, making it possible to follow the mechanical response associated with the photo-reticulation of a solution (sol-gel transition) as well as to optionally observe optically a reticulation occurring without UV radiation.

According to a preferred practical embodiment emerging from FIG. 2 in particular, the frame that forms a box can be composed of two half-shells 5 and 5' assembled together (in a removable and pressurized manner), constituting a housing for receiving, by additional cooperation, two recesses 10, 10' each of which holds, preferably in a clamped manner, a sample-holder blade 2, 2'/associated piezoelectric ceramic element (s) 4, 4' arrangement, and, optionally, one or more shield part(s) 6 and/or parts for bracing and electric insulation 8. Said two half-shells 5 and 5' are assembled under pressure with a tightening screw 11, several, preferably three, adjusting counter-screws 12, advantageously with micrometric adjustment control, being provided on one of the two half-shells 5 or 5' for the purpose of the adjustment of the parallelism between the faces opposite the latter and calibrated spacers optionally being placed between the faces opposite said two half-shells 5, 5' based on the thicknesses of the above-mentioned arrangements and that of the sample 3 to be analyzed.

The assembly glue(s) of the various components can consist of epoxy glues, if necessary charged or filled with a metal (for example silver) to make them electrically conductive.

As emerges from FIGS. 9A and 9B of the accompanying drawings, the ceramic elements 4 and 4' can be grounded at their faces in contact with the corresponding sample-holder blade 2, 2', just like the respectively concerned faces of said blades 2 and 2'.

For this purpose, the blades 2 and 2' can comprise a conductive track for common grounding, making it possible to take measurements with zero electric field at the sample 3.

As a variant, it is also possible to ground the ceramic elements 4 and 4' at their faces opposite to those in contact with the respective sample-holder blades 2, 2' (indicated by way of example in dotted lines in FIG. 9B).

In this variant, it will be possible to take measurements with application of an electric field (for example under-field flow analysis).

It will also be possible to polarize the two emitting ceramics 4 in reverse one relative to the other, to apply a differential excitation signal to the sample.

Figure 4:
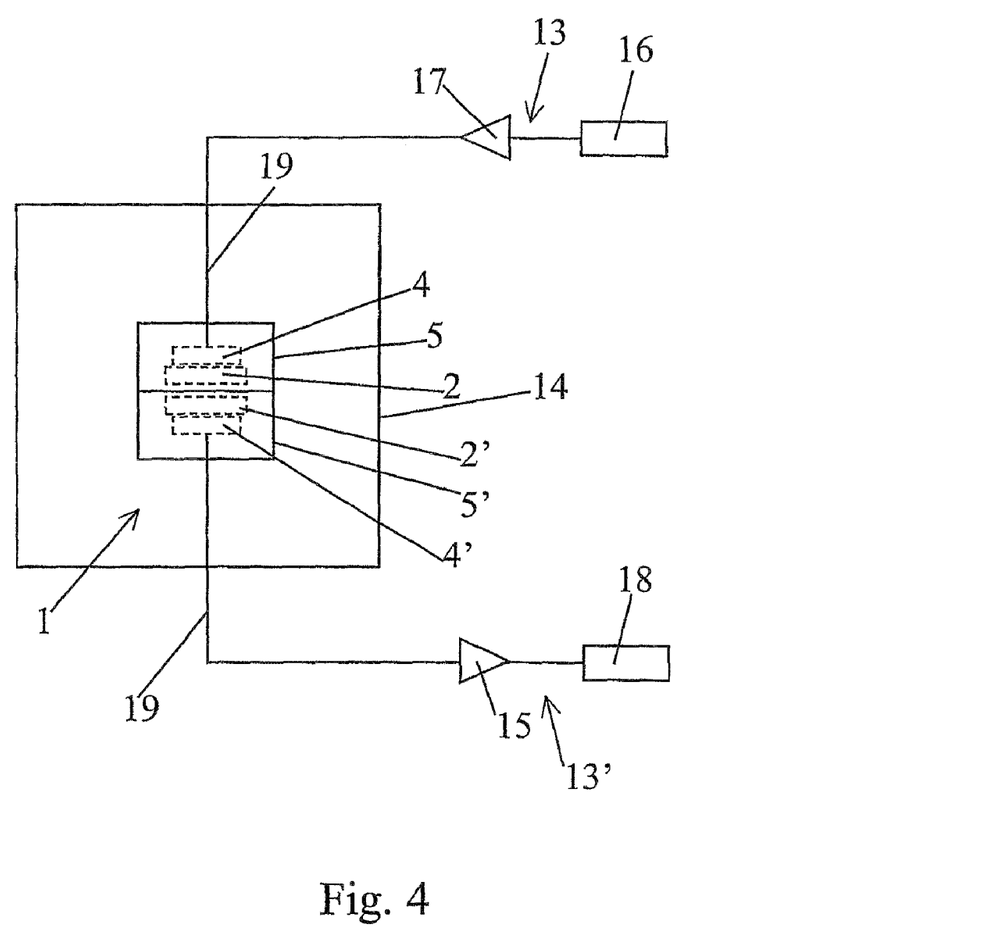
FIG. 4 is a schematic representation of a piezorheometer according to the invention.

The invention also has as its object a measuring instrument, preferably portable, of the piezorheometer type, comprising a measuring cell that receives the sample 3 to be analyzed and that comprises piezoelectric ceramic elements for emission 4 and for receiving 4', a feed chain 13 functionally connected to emitting or emission piezoelectric ceramic(s) 4 and a measuring chain 13' that is connected functionally to receiving or reception piezoelectric ceramic(s) 4'. This instrument is essentially characterized in that the measuring cell consists of a measuring cell 1 as described above.

The feed chain 13 comprises, for example, an excitation signal generator 16 feeding, optionally via an amplification means 17, the emitting ceramic element(s) 4, and the measuring chain 13' essentially consists of an amplification means 15 receiving the signals that are delivered by the receiving ceramic element(s) 4', whereby the output of said means 15 is connected to a unit 18 for processing and exploitation of said amplified measuring signals, optionally after conversion, for example in the form of a computer unit that may or may not be coupled to an oscilloscope. This unit 18 can also integrate preprogrammed or parameterized software making it possible to calibrate the piezorheometer and to compensate for or to correct the drifts, variations, interferences or the like that can influence the results of the measurement. This unit 18 can also manage the operation of the entire measuring instrument and can be equipped with interfaces for display, editing and programming.

So as to make possible rheological measurements under pressure, the measuring cell 1 is advantageously placed in a closed chamber in a sealed manner, preferably in the form of a box 14, whose internal pressure and temperature can be fixed or varied in a controlled fashion within predefined ranges (FIG. 4).

Thus, the production of a specific chamber designed to receive the cell or cells 1 of the piezorheometer makes it possible to take theological measurements under pressure on the order of 1 kbar and more.

According to a characteristic of the invention, the said piezorheometer-type measuring instrument comprises, on the one hand, a means for compensating for or correcting the phase shift or the parasitic time shift induced by the feed chains 13 and by the measuring chains 13' in particular by the means for amplification 15 of the measuring signal delivered by the second piezoelectric ceramic element(s) 4' that is stuck on the receiving sample-holder blade 2', and, on the other hand, a means for correcting or compensating for gain variations of said chains 13, 13', in particular said amplification means 15, and this as a function of the frequency of the excitation signal delivered by the feed chain 13.

Figure 5:
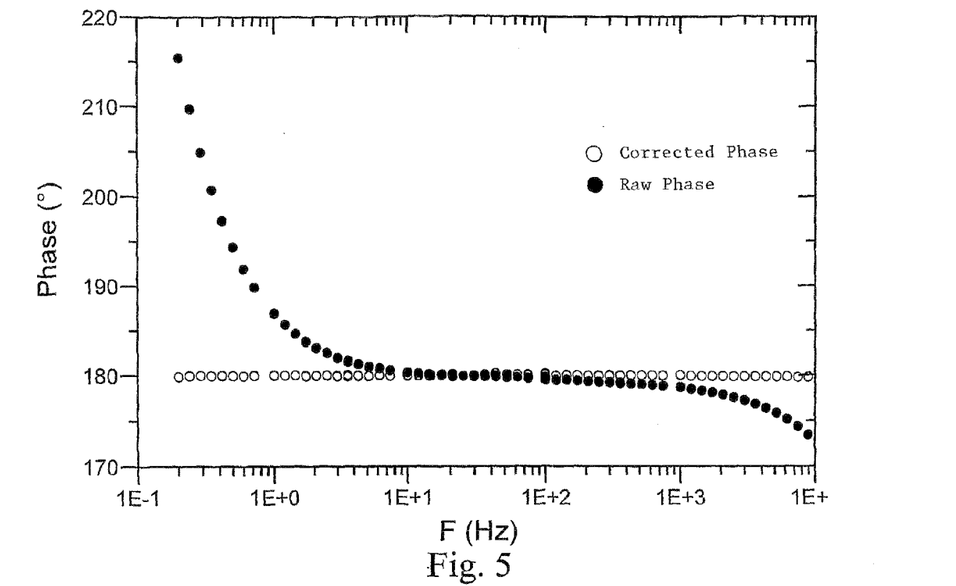
FIGS. 5 and 6 show the frequency variations of the corrections respectively of the phase and the gain of the measuring chain forming part of the piezorheometer according to the invention.
Figure 6:
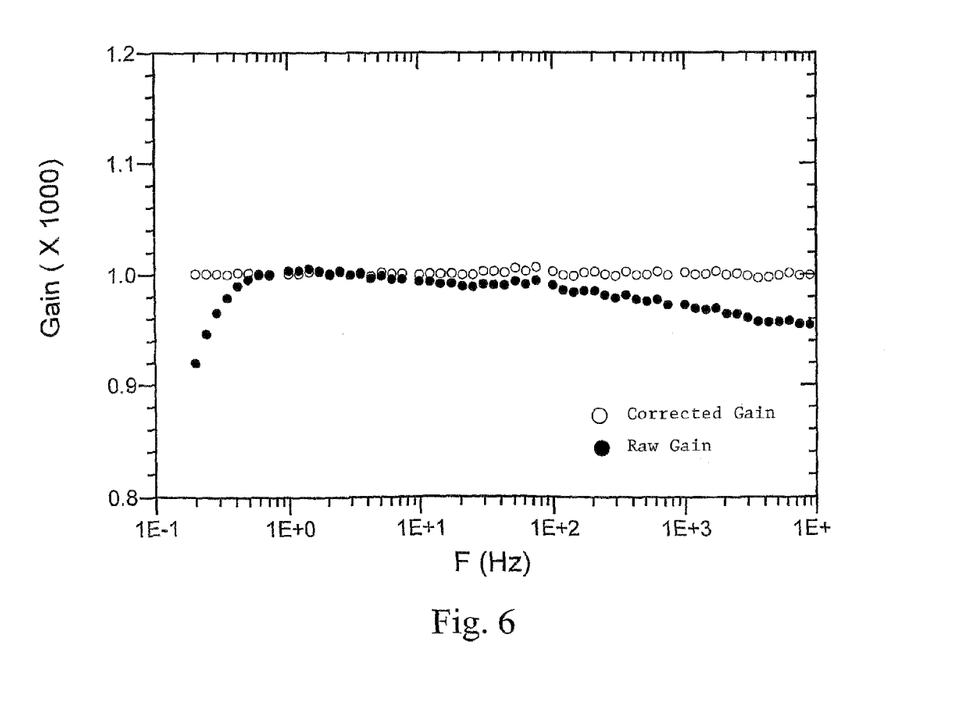
Figure 7:
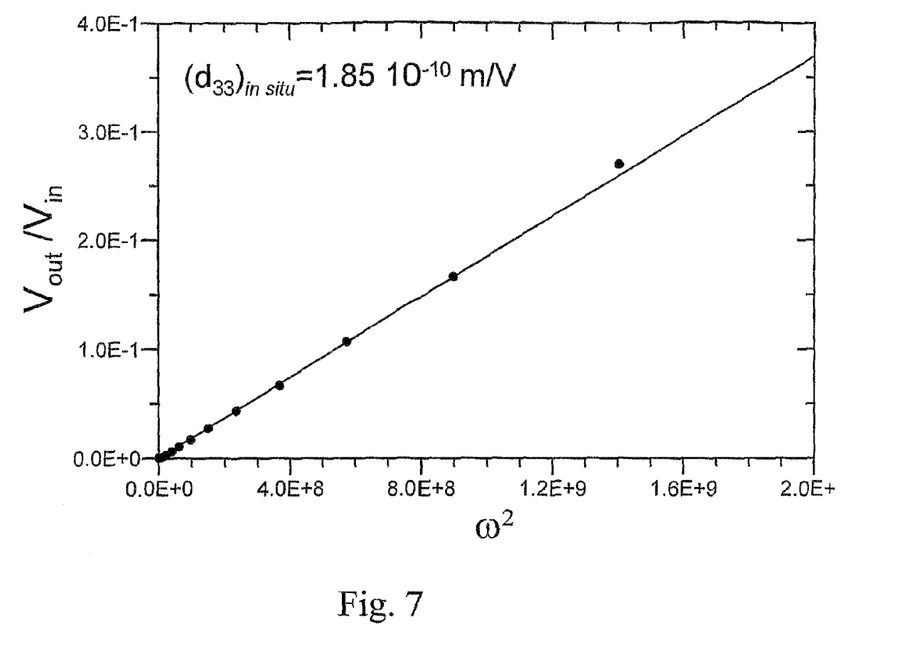
FIG. 7 shows the curve for determining the piezoelectric constant of a compression ceramic element.

These means for correction and compensation advantageously come in the form of software means or calculating means used at the unit 18, standardized in a preliminary calibration phase after determination of effective drifts in terms of gain and phase of the feed chain 13 and the measuring chain 13' (see the curves of FIGS. 5 and 6).

Finally, the invention also has as its object a process for measuring properties or physical or mechanical characteristics of samples of solid, liquid or intermediate-type materials (for example, gels and elastomers) by means of an instrument as described above.

This process is characterized in that it consists, before implementing said instrument, in carrying out preliminary operations of standardization and calibration comprising at least one, preferably several, of the following operations:

The adjustment of the parallelism between the sample-holder blades 2 and 2', The adjustment of the spacing between the two half-shells 5, 5' that constitute the frame, based in particular on the thickness of the sample 3 to be analyzed, The determination and the recording of the variation function of the phase between excitation signal and measuring signal as a function of frequency, The determination and the recording of the variation function of the gain of the feed chains 13 and measuring chain 13' as a function frequency, The determination and the recording of the thermal expansion/retraction function of the measuring cell 1, The determination and the recording of the piezoelectric constant of the ceramic elements 4, 4' that are made integral with or stuck on the sample-holder blades 2, 2'.

The recording of the various determined data is carried out at the unit 18.

The adjustment of the parallelism can be carried out either with the aid of calibrated spacers or by optical interferometry.

In the case of a liquid, the variation of the thickness of the measuring cell 1 can be carried out either:

By calibrated spacers of decreasing thickness (for example 100 μm, 50 μm, and 20 μm) when it is known in advance what the thicknesses are of sample 3 that it is desired to study;

By micrometric screws that make it possible to vary continuously the thickness of the sample. A cell 1 using these screws has a reduction of the high-frequency part of the usable frequency range, in consequence of a reduction in the rigidity of the frame of the cell.

The determination of the piezoelectric shear or compression constant of each ceramic element 4, 4' is made in situ, after gluing said element to its corresponding blade 2 or 2'.

This determination can be made by means of a calibrated accelerometer with a vibrating blade maintained by an electric motor. This accelerometer also makes it possible to verify the polarization direction of the measured ceramic element.

A practical embodiment of a measuring cell 1 and a piezorheometer comprising at least one such cell according to the invention are described below in a more detailed manner and in connection with the FIGS. 2, 3, and 4.

As FIG. 2 shows, such a cell 1 essentially consists of two half-shells or half-boxes 5 and 5', assembled by tightening screws 11. The piezoelectric ceramics 4, 4' are glued to a silica glass washer 8, itself glued in the housing 10, 10' of each half-box 5, 5'. The role of this washer 8 is to insulate electrically the ceramics from the frame made in steel or in a similar conductive rigid material. The sample-holder blades 2, 2' are glued to the other face of the ceramic elements 4, 4'. Coaxial cables 19 make it possible to bring in and to receive the excitation signals, receiving signals or measuring signals. A metallic blade 6, placed between the frame and the sample-holder blades, has as its object to reduce the electrostatic radiation due to the fact that the ceramics for emission and reception are close to one another. Adjustment counter-screws 12, or micrometric screws, make it possible to adjust the air gap (distance between the blades 2 and 2') of the cell 1 (from 10 microns to one millimeter), the parallelism between the blades being verified optically thanks to the openings 9 and 9' that extend through the portions of box 5, 5', the element 8 and between the ceramic elements 4, 4' (zero ceramic element in the center of the blade 2 or 2').

These openings 9 and 9' also make possible a direct measurement of the thickness of the sample with a micrometer, the thickness of the sample-holder blades being determined in advance. They also make it possible either to observe the sample 3 directly or to irradiate the latter with UV radiation, for example. The small size of the measuring cell 1 makes it possible to place it in the optical path of a microscope, thus making possible an observation of the sample on a smaller scale.

The frame 5, 5' of the cell is generally made of invar steel but it can also be made of other materials such as stainless steel or brass for measurements in a magnetic field. The cell can be placed in an oven (not shown in the figure), which makes it possible to carry out measurements between −60° C. and 180° C. The oven is controlled by a heat regulator connected to the control unit 18 or computer, and the temperature of the sample is measured by a digital thermometer that is also connected to the computer. These arrangements make possible an automation of experiments; the temperature can be changed in successive stages, and, for each temperature, the mechanical properties of the sample can be determined as a function of frequency.

Among the advantages of the cell and the piezorheometer that take into account the various characteristics according to the invention, it is possible to cite in particular and in a nonlimiting fashion the following:

The large frequency range that is accessible ($10^{-2}$ Hz-$10^4$ Hz),

The possibility of varying the thickness of the sample in a controlled fashion between ~10 μm and ~100 μm, The very weak strains that are imposed ($10^{-6}$-$10^{-3}$), The monitoring of boundary conditions on the walls in contact with the sample (zero or non-zero velocity), The possibility of studying oriented materials (liquid crystals) by treating the glass blades with a suitable surfactant, The possibility of optically observing the structure of the sample during the mechanical measurements, The possibility of irradiating the sample (photo-reticulation, for example) and of following a gelling process, The compact dimensions of the cell (Ø=6 cm; h=3 cm) that make it possible to place it in a confined space (air gap of an electromagnet; space shuttle) or to make it a portable rheometer, The small amount of product necessary (<30 mg), which makes it possible to study biological substances, The possibility of studying soft solids (elastomers, gels) under static precompression, The possibility of conducting rheology under pressure (1 kbar), The reduced cost for an instrument that operates without pressure.

Of course, the invention is not limited to the embodiment described and shown in the accompanying drawings. Modifications remain possible, in particular from the standpoint of the composition of the various elements or by substitution of technical equivalents, without thereby exceeding the field of protection of the invention.

The invention claimed is:

1. A shear or compression piezorheometer cell, comprising:
    two sample-holder blades (2, 2') that clamp between them a sample (3) to be analyzed,
    piezoelectric ceramic elements (4, 4') relative to the faces of the blades that are opposite to the faces in contact with the sample, and
    a frame (5, 5') that keeps the arrangement of blades and ceramic elements compressed,
    wherein at least one said ceramic element (4), denoted emitting ceramic below, is stuck to or made cohesive with one of the two blades or emitting blade and subjects the latter to shear or compression vibrations under the action of an excitation signal, and at least one said ceramic element (4'), denoted receiving ceramic below, is stuck to or made cohesive with the other blade or receiving blade and transforms the constraints or stress to which the latter is subjected into a measuring signal,
    wherein the emitting and receiving ceramics are placed so that the respective polarizations of the emitting ceramic (4) and the receiving ceramic (4'), or the respective resulting polarizations of the emitting ceramics (4) and receiving ceramics (4') are parallel,
    wherein said respective polarizations are of the same direction,
    wherein the sample-holder blades (2, 2') have an increased thickness, and
    wherein one or more shield part(s) (6), designed to limit the electrostatic radiation and the electrostatic coupling that results between the emitting ceramic(s) (4) and the receiving ceramic(s) (4'), are mounted in the frame (5, 5'), and
    further comprising an additional covering blade (2") that is removably attached to at least one of the sample-holder blades, wherein at the level of a face of the additional covering blade (2") in contact with the sample (3) to be analyzed, the sample-holder blades (2 and 2') comprise a surface treatment that prevents or promotes the sliding of the sample (3) or orients the sample at the level of said face in contact with the sample.

2. Measuring cell according to claim 1, wherein one or each of the two sample-holder blades (2 and 2') is provided, on its face turned toward the sample (3), with a layer or a coating (2") that is removably added or attached to this blade (2 and 2').

3. Measuring cell according to claim 1, wherein the assembly formed by the frame (5, 5') with, mounted therein, the piezoelectric ceramic elements (2, 2') has a perforated structure comprising two opposite openings (9, 9') for observation and irradiation of the sample (3) extending respectively from the outside of the frame (5, 5') up to the sample-holder blades (2, 2').

4. Measuring cell according to claim 1, wherein the frame that forms a box is composed of two half-shells (5 and 5') assembled together, constituting a housing for receiving, by additional cooperation, two recesses (10, 10') each of which holds a sample-holder blade (2, 2')/associated piezoelectric ceramic element(s) (4, 4') arrangement, wherein said two half-shells (5 and 5') are assembled under pressure with a tightening screw (11), several adjusting counter-screws (12) being provided on one of the two half-shells (5 or 5') for the purpose of the adjustment of the parallelism between the faces opposite the latter.

5. Measuring cell according to claim 1, wherein the ceramic elements (4 and 4') are grounded at their faces in contact with the corresponding sample-holder blade (2, 2'), just like the respectively concerned faces of said blades (2 and 2').

6. Measuring cell according to claim 1, wherein the ceramic elements (4 and 4') are grounded at their faces that are opposite to those in contact with the respective sample-holder blades (2, 2').

7. Measuring cell according to claim 1, wherein the shield part or each shield part (6) designed to reduce or to eliminate the radiation and the electrostatic coupling that results therefrom comprises a jacket, a plate or a metal blade, placed between the emitting blade (2) or the receiving blade (2') and the frame (5, 5').

8. Measuring cell according to claim 7, wherein one or each of the two sample-holder blades (2 and 2') is provided, on its face turned toward the sample (3), with a layer or a coating (2") that is removably added or attached to this blade (2 and 2').

9. Measuring cell according to claim 1, wherein the ceramics (4, 4') are added to the respective sample-holder blades (2 and 2') by gluing or welding and are each assembled with the frame (5, 5') by gluing or welding, the bonding and assembly adhesives preserving their adhesive property and their rigidity in a temperature range of −60° C. to +180° C.

10. Measuring cell according to claim 9, wherein the material or materials for bonding and assembly, the material constituting the frame (5, 5'), all have thermal expansion/retraction factors that are essentially of the same value as the thermal expansion/retraction factor of the material that constitutes the sample-holder blades (2, 2').

11. A portable, piezorheometer-type measuring instrument, comprising:
    a measuring cell receiving the sample to be analyzed;
    piezoelectric ceramic elements for emission and for receiving;
    a feed chain that is functionally connected to emitting or emission piezoelectric ceramics and a measuring chain that is connected functionally to receiving or reception piezoelectric ceramic(s),
    the measuring cell, comprising, two sample-holder blades (2, 2') that clamp between them the sample (3) to be analyzed, piezoelectric ceramic elements (4, 4') relative to the faces of the blades that are opposite to the faces in contact with the sample, and a frame (5, 5') that keeps the arrangement of blades and ceramic elements compressed, wherein at least one said ceramic element (4), denoted emitting ceramic below, is stuck to or made cohesive with one of the two blades or emitting blade and subjects the latter to shear or compression vibrations under the action of an excitation signal, and at least one said ceramic element (4'), denoted receiving ceramic below, is stuck to or made cohesive with the other blade or receiving blade and transforms the constraints or stress to which the latter is subjected into a measuring signal, wherein the emitting and receiving ceramics are placed so that the respective polarizations of the emitting ceramic (4) and the receiving ceramic (4'), or the respective resulting polarizations of the emitting ceramics (4) and receiving ceramics (4') are parallel, wherein said respective polarizations are of the same direction, wherein the sample-holder blades (2, 2') have an increased thickness, wherein one or more shield part(s) (6), designed to limit the electrostatic radiation and the electrostatic coupling that results between the emitting ceramic(s) (4) and the receiving ceramic(s) (4'), are mounted in the frame (5, 5'), the measuring instrument further comprising means for compensating for or correcting the phase shift or the parasitic time shift induced by the feed chains (13) and measuring chains (13') by the means for amplification (15) of the measuring signal delivered by the second piezoelectric ceramic element(s) (4') stuck on or made cohesive with the receiving sample-holder blade (2'), and means for correcting or compensating for gain variations of said chains (13, 13') as a function of the frequency of the excitation signal delivered by the feed chain (13).

12. Instrument according to claim 11, wherein the measuring cell (1) is placed in a closed chamber in a sealed manner.

13. Process for measuring properties or physical or mechanical characteristics of samples of solid, liquid or intermediate-type materials by means of an instrument according to claim 11, comprising, before using said instrument, carrying out preliminary operations of standardization and calibration including at least one of the following operations:

adjustment of the parallelism between the sample-holder blades (2 and 2'), adjustment of the spacing between the two half-shells (5, 5') that constitute the frame, based on the thickness of the sample (3) to be analyzed, determination and the recording of the variation function of the phase between excitation signal and measuring signal as a function of frequency, determination and the recording of the variation function of the gain of the feed chains (13) and measuring chains (13') as a function of frequency, determination and the recording of the thermal expansion/retraction function of the measuring cell (1), and determination and the recording of the piezoelectric constant of the ceramic elements (4, 4') that are stuck on or made cohesive with the sample-holder blades (2, 2').

14. Process for measuring properties or physical or mechanical characteristics of samples of solid, liquid or intermediate-type materials by means of an instrument according to claim 12, comprising, before using said instrument, carrying out preliminary operations of standardization and calibration including at least one of the following operations:

adjustment of the parallelism between the sample-holder blades (2 and 2'), adjustment of the spacing between the two half-shells (5, 5') that constitute the frame, based on the thickness of the sample (3) to be analyzed, determination and the recording of the variation function of the phase between excitation signal and measuring signal as a function of frequency, determination and the recording of the variation function of the gain of the feed chains (13) and measuring chains (13') as a function of frequency, determination and the recording of the thermal expansion/retraction function of the measuring cell (1), and determination and the recording of the piezoelectric constant of the ceramic elements (4, 4') that are stuck on or made cohesive with the sample-holder blades (2, 2').

15. A shear or compression piezorheometer cell, comprising:

two sample-holder blades (2, 2') that clamp between them a sample (3) to be analyzed, piezoelectric ceramic elements (4, 4') relative to the faces of the blades that are opposite to the faces in contact with the sample, and, a frame (5, 5') that keeps the arrangement of blades and ceramic elements compressed, wherein at least one said ceramic element (4), denoted emitting ceramic below, is stuck to or made cohesive with one of the two blades or emitting blade and subjects the latter to shear or compression vibrations under the action of an excitation signal, and at least one said ceramic element (4'), denoted receiving ceramic below, is stuck to or made cohesive with the other blade or receiving blade and transforms the constraints or stress to which the latter is subjected into a measuring signal, wherein the emitting and receiving ceramics are placed so that the respective polarizations of the emitting ceramic (4) and the receiving ceramic (4'), or the respective resulting polarizations of the emitting ceramics (4) and receiving ceramics (4') are parallel, wherein said respective polarizations are of the same direction, wherein the sample-holder blades (2, 2') have an increased thickness, wherein one or more shield part(s) (6), designed to limit the electrostatic radiation and the electrostatic coupling that results between the emitting ceramic(s) (4) and the receiving ceramic(s) (4'), are mounted in the frame (5, 5'), and wherein the emitting sample-holder blade (2) has a protuberance forming piston (7) at its face in contact with the sample (3), the sample layer (3) that is located between the front face (7') of the protuberance (7) and the smooth and flat face of the receiving sample-holder blade (2') forming the analyzed sample part.

16. Measuring cell according to claim 15, wherein the shield part or each shield part (6) designed to reduce or to eliminate the radiation and the electrostatic coupling that results therefrom comprises a jacket, a plate or a metal blade, placed between the emitting blade (2) or the receiving blade (2') and the frame (5, 5').

17. Measuring cell according to claim 15, wherein one or each of the two sample-holder blades (2 and 2') is provided, on its face turned toward the sample (3), with a layer or a coating (2") that is removably added or attached to this blade (2 and 2').

18. Measuring cell according to claim 15, wherein the assembly formed by the frame (5, 5') with, mounted therein, the piezoelectric ceramic elements (2, 2') has a perforated structure comprising two opposite openings (9, 9') for observation and irradiation of the sample (3) extending respectively from the outside of the frame (5, 5') up to the sample-holder blades (2, 2').

19. Measuring cell according to claim 15, wherein the frame that forms a box is composed of two half-shells (5 and 5') assembled together, constituting a housing for receiving, by additional cooperation, two recesses (10, 10') each of which holds a sample-holder blade (2, 2')/associated piezoelectric ceramic element(s) (4, 4') arrangement, wherein said two half-shells (5 and 5') are assembled under pressure with a tightening screw (11), several adjusting counter-screws (12) being provided on one of the two half-shells (5 or 5') for the purpose of the adjustment of the parallelism between the faces opposite the latter.

20. Measuring cell according to claim 15, wherein the ceramic elements (4 and 4') are grounded at their faces in contact with the corresponding sample-holder blade (2, 2'), just like the respectively concerned faces of said blades (2 and 2').

21. Measuring cell according to claim 15, wherein the ceramic elements (4 and 4') are grounded at their faces that are opposite to those in contact with the respective sample-holder blades (2, 2').

22. Measuring cell according to claim 15, wherein the ceramics (4, 4') are added to the respective sample-holder blades (2 and 2') by gluing or welding and are each assembled with the frame (5, 5') by gluing or welding, the bonding and assembly adhesives preserving their adhesive property and their rigidity in a temperature range of −60° C. to +180° C.

23. Measuring cell according to claim 22, wherein the material or materials for bonding and assembly, the material constituting the frame (5, 5'), all have thermal expansion/retraction factors that are essentially of the same value as the thermal expansion/retraction factor of the material that constitutes the sample-holder blades (2, 2').

24. A shear piezorheometer cell, comprising:
two sample-holder blades (2, 2') that clamp between them a sample (3) to be analyzed,
piezoelectric ceramic elements (4, 4') relative to the faces of the blades that are opposite to the faces in contact with the sample, and,
a frame (5, 5') that keeps the arrangement of blades and ceramic elements compressed,
wherein at least one said ceramic element (4), denoted emitting ceramic below, is stuck to or made cohesive with one of the two blades or emitting blade and subjects the latter to shear vibrations under the action of an excitation signal, and at least one said ceramic element (4'), denoted receiving ceramic below, is stuck to or made cohesive with the other blade or receiving blade and transforms the stress to which the latter is subjected into a measuring signal,
wherein the emitting and receiving ceramics are placed so that the respective polarizations of the emitting ceramic (4) and the receiving ceramic (4'), or the respective resulting polarizations of the emitting ceramics (4) and receiving ceramics (4') are parallel,
wherein said respective polarizations are of the same direction,
wherein the sample-holder blades (2, 2') have an increased thickness,
wherein one or more shield part(s) (6), designed to limit the electrostatic radiation and the electrostatic coupling that results between the emitting ceramic(s) (4) and the receiving ceramic(s) (4'), are mounted in the frame (5, 5'), and
wherein each ceramic element for emission (4) and for reception (4') comprises a stacking of two ceramics having orthogonal polarization directions in the median plane of said measuring cell (1).

25. Measuring cell according to claim 24, wherein the shield part or each shield part (6) designed to reduce or to eliminate the radiation and the electrostatic coupling that results therefrom comprises a jacket, a plate or a metal blade, placed between the emitting blade (2) or the receiving blade (2') and the frame (5, 5').

26. Measuring cell according to claim 24, wherein one or each of the two sample-holder blades (2 and 2') is provided, on its face turned toward the sample (3), with a layer or a coating (2") that is removably added or attached to this blade (2 and 2').

27. Measuring cell according to claim 24, wherein the assembly formed by the frame (5, 5') with, mounted therein, the piezoelectric ceramic elements (2, 2') has a perforated structure comprising two opposite openings (9, 9') for observation and irradiation of the sample (3) extending respectively from the outside of the frame (5, 5') up to the sample-holder blades (2, 2').

28. Measuring cell according to claim 24, wherein the frame that forms a box is composed of two half-shells (5 and 5') assembled together, constituting a housing for receiving, by additional cooperation, two recesses (10, 10') each of which holds a sample-holder blade (2, 2')/associated piezoelectric ceramic element(s) (4, 4') arrangement, wherein said two half-shells (5 and 5') are assembled under pressure with a tightening screw (11), several adjusting counter-screws (12) being provided on one of the two half-shells (5 or 5') for the purpose of the adjustment of the parallelism between the faces opposite the latter.

29. Measuring cell according to claim 24, wherein the ceramic elements (4 and 4') are grounded at their faces in contact with the corresponding sample-holder blade (2, 2'), just like the respectively concerned faces of said blades (2 and 2').

30. Measuring cell according to claim 24, wherein the ceramic elements (4 and 4') are grounded at their faces that are opposite to those in contact with the respective sample-holder blades (2, 2').

31. Measuring cell according to claim 24, wherein the ceramics (4, 4') are added to the respective sample-holder blades (2 and 2') by gluing or welding and are each assembled with the frame (5, 5') by gluing or welding, the bonding and assembly adhesives preserving their adhesive property and their rigidity in a temperature range of −60° C. to +180° C.

32. Measuring cell according to claim 31, wherein the material or materials for bonding and assembly, the material constituting the frame (5, 5'), all have thermal expansion/retraction factors that are essentially of the same value as the thermal expansion/retraction factor of the material that constitutes the sample-holder blades (2, 2').

* * * * *